June 9, 1959 H. KLEINE Plant Pat. 1,844
EUROPEAN SMOKE TREE
Filed Oct. 28, 1958
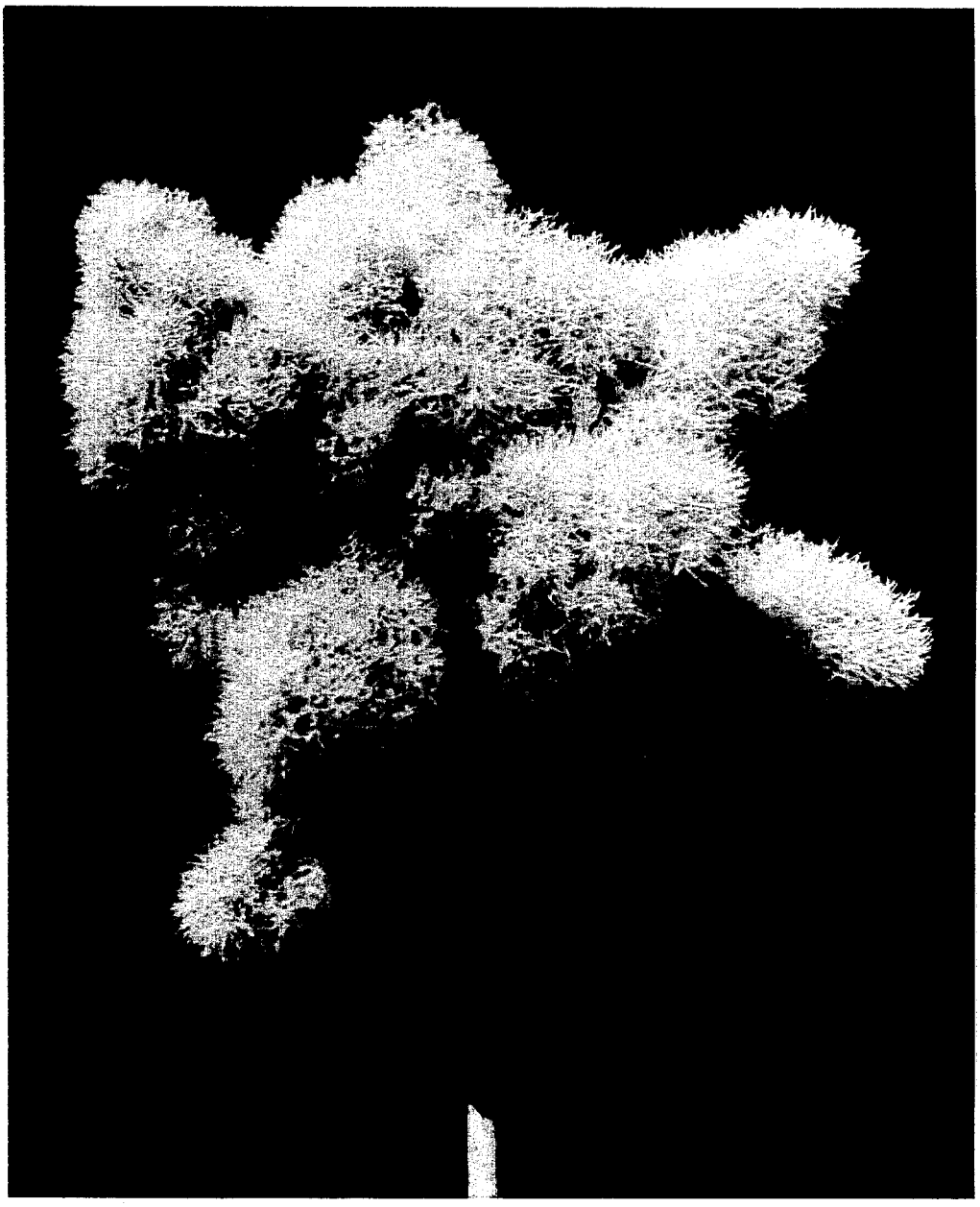
INVENTOR
Henry Kleine
By Orville M. Kile
Plant Patent Agt United States Patent Office Plant Pat. 1,844
Patented June 9, 1959

1,844

EUROPEAN SMOKE TREE

Henry Kleine, Newport, Mich.

Application October 28, 1958, Serial No. 770,247

1 Claim. (Cl. 47—59)

My present discovery pertains to a new and improved variety of ornamental shrubs known popularly as European smoke tree, having to do particularly with the panicles of the shrub.

This new variety is a seedling of the variety *Cotinus coggygria* and is the result of selection by me from thousands of seedlings planted and observed by me at my nurseries near Newport, Michigan, over the past 12 years. If differs principally from other varieties because of the color, quantity, type, and length of season of the decorative panicles. The fluffy panicles are of striking color, beginning with a color between Chamois (Plate XXX) and Yellow Ochre (Plate XV) sometimes tinged with rust, and turning to soft green, approximately Absinthe Green (Pl. XXXI), with a pink cast which becomes more pronounced as the season advances.

Because the plant is more floriferous and its panicles more downy and compact than those of the usual varieties, the foliage is almost completely covered, whereas the usual tree or shrub is covered only at the top. These panicles persist through an unusually long period.

The variety grows more slowly and is semi-dwarf, which causes it to present a neater appearance than the rank-growing varieties. It is practically seedless, producing only an occasional seed.

I have asexually reproduced this new variety at my nurseries in Michigan, by means of cuttings and layers, and its outstanding features appear to be permanent.

The accompanying illustrations show a portion of a plant of this new variety in approximately its true colors at its typical full-blown stage of coloring.

Following is a more detailed description in which color plate references indicate Ridgway's Color Standards and Nomenclature. Where no plate number is mentioned the ordinary dictionary meaning of the term is intended.

Type of plant: Woody, ornamental shrub; deciduous.

Growth: Upright; compact; slow-growing; semi-dwarf.

Cold resistance: Hardy in this area, although the plants prefer a sheltered position.

Blooming period: June 15 to July 25 in this climate, which is a much longer period than for any other known variety.

Blooming habit: The plant blooms each year and is exceedingly prolific, the resulting panicles covering the foliage of the entire plant.

Individual flowers: Small, with 5 petals, 5 short stamens and 3 short styles. Sterile, with only an occasional seed.

Panicles: Composed of many small sterile flowers, later of downy balls.

*Form.*—After the dropping of the petals, the pedicles lengthen and are covered with numerous long hairs, thus becoming downy and globular. (In contrast with the usual open and straggly form.)

*Color.*—Panicles go through phases of color, changing as the season progresses. After petals have dropped, the panicles on a typical plant of this variety begin with a color approximately chamois, turn to soft green, and gradually develop a delicate pink tinge to the green, becoming more pronounced as the panicles mature.

Fruit: Small, insignificant and asymmetrical drupelet.

Leaves:

*Occurrence.*—In clusters, and irregularly along long stems.

*Size.*—Small.

*Shape.*—Narrow oval to obovate; entire.

*Aspect.*—Smooth.

*Color.*—Light green.

Having thus disclosed my discovery, I claim:

The new and improved variety of European smoke tree, substantially as herein shown and described, characterized particularly by its slow growth; its semi-dwarf form; its regularity of bloom each year; its long season of production of panicles with only an occasional seed; and the compact, downy nature of the panicles of distinctive, striking color which changes from chamois through soft green after which a delicate pink tinge is added to the soft green.

No references cited.